United States Patent
Liu et al.

(10) Patent No.: US 7,666,887 B2
(45) Date of Patent: *Feb. 23, 2010

(54) STABLE, NEUTRAL PH, VOC-FREE BIOCIDAL COMPOSITIONS OF 1,2-BENZISOTHIAZOLIN-3-ONE

(75) Inventors: Xianbin Liu, Basking Ridge, NJ (US); Karen Winkowski, Sayreville, NJ (US)

(73) Assignee: ISP Investments, Inc., Wilmington, DE (US)

( * ) Notice: Subject to any disclaimer, the term of this patent is extended or adjusted under 35 U.S.C. 154(b) by 779 days.

This patent is subject to a terminal disclaimer.

(21) Appl. No.: 11/519,641

(22) Filed: Sep. 12, 2006

(65) Prior Publication Data

US 2007/0010567 A1 Jan. 11, 2007

Related U.S. Application Data

(63) Continuation of application No. 10/818,890, filed on Apr. 6, 2004, now Pat. No. 7,105,555.

(51) Int. Cl.
*A01N 43/80* (2006.01)
*C07D 275/04* (2006.01)

(52) U.S. Cl. ...................... 514/373; 548/209
(58) Field of Classification Search ................. 514/373
See application file for complete search history.

(56) References Cited

U.S. PATENT DOCUMENTS 4,188,376 A * 2/1980 Payne et al. ................. 514/373

* cited by examiner

*Primary Examiner*—Sreeni Padmanabhan
*Assistant Examiner*—Layla Soroush
(74) *Attorney, Agent, or Firm*—William J. Davis

(57) ABSTRACT

What is described herein is a neutral pH, VOC-free biocidal composition of 1,2-benzisothiazolin-3-one which is stable at low temperatures for an extended period of time. The compositions are particularly advantageous in use in protecting latex, paint, coating, cosmetic and personal care formulations against microbiological spoilage.

1 Claim, No Drawings

STABLE, NEUTRAL PH, VOC-FREE BIOCIDAL COMPOSITIONS OF 1,2-BENZISOTHIAZOLIN-3-ONE

This is a continuation of application Ser. No. 10/818,890, filed on Apr. 6, 2004, now U.S. Pat. No. 7,105,555.

BACKGROUND OF THE INVENTION

1. Field of the Invention

This invention relates to biocidal compositions of 1,2-benzisothiazolin-3-one (BIT) and, more particularly, to stable, VOC-free compositions of BIT which have a neutral pH which is particularly advantageous in use in latex, paint, coating, cosmetic and personal care products.

2. Description of the Prior Art 1,2-benzisothiazolin-3-one (referred to hereinafter as BIT) is an established industrial biocide and is particularly effective in protecting aqueous media against microbiological spoilage. It is particularly effective as a bactericide and is especially suited to the protection of lattices. Thus one of its major uses is as an in-can preservative for the preservation of acrylic and acrylate paint emulsions.

BIT has low aqueous solubility and can cause sensitization in some individuals. Consequently, for ease of handling and to reduce handling risks, it has been formulated as an aqueous dispersion and also as a stable solution in an amine solvent as disclosed in UK Patents 1,191,253 and UK 1,330,531. For some applications, these amine formulations are not attractive and are rarely used for indirect food contact applications, such as for instance for use in water-based adhesives which may be used in the food packaging industry, because the amines are volatile and tend to have an unpleasant odor. Furthermore, amine solutions of BIT may not be suitable for use as biocides in in-can preservation of lattices because amine solvents may cause yellowing of the latex. Amines are also capable of reacting with and deactivating certain biocides and this further limits the use of amine formulations of BIT when used with such biocides.

To avoid these problems associated with amines, BIT is now generally formulated as an alkali metal salt in one or more water miscible solvents such as dipropylene glycol as disclosed in U.S. Pat. No. 4,188,376. Such formulations are stable solutions which withstand freeze-thaw temperature cycling, and, even if frozen recover on warming to regenerate a stable solution. Formulations of this type containing 20% BIT, and 65% dipropylene glycol, the remainder being water, wherein the BIT has been converted to sodium-BIT by reacting 1.1 moles sodium hydroxide with 1 mole BIT as described in Example 1 of said U.S. Pat. No. 4,188,376 have been available commercially for many years as Proxel® GXL (Proxel is a registered trademark of Avecia).

A disadvantage of such formulations is their high pH, normally pH 12 or above, which can cause "pH-shock" and coagulation when added to a medium to be protected, such as an emulsion paint or latex, owing to the different pH of the medium. The high pH is caused by the combination of the amount and type of solvent employed and also the amount of alkali both of which have hitherto been considered necessary to produce stable solutions of sodium-BIT. Indeed, in all the working examples of U.S. Pat. No. 4,188,376 a 10% excess of sodium hydroxide has been used relative to BIT in making the sodium salt.

U.S. Pat. No. 5,558,816 described a BIT composition using dipropylene glycol as the solvent. These compositions had a lower pH (8.9-10) and a lower viscosity (60-180 m Pa·s) than commercial products. However, dipropylene glycol is a volatile solvent and it contributed greatly to the high VOC of the composition.

U.S. Pat. No. 5,585,033 described BIT compositions which contained one or more polyglycol triols, e.g. glycerol ethoxylate or glycerol propoxylate, as the organic solvent, optionally including an organic cosolvent.

U.S. Pat. No. 6,361,788 described BIT compositions free of 5-chloro-2-methylisothiazolin-3-one.

WO 95/00019 described a BIT formulation containing xanthan gum and a dispersant which was free of organic solvents.

Accordingly, it is an object of this invention to provide a new and improved BIT composition which is stable, has a neutral pH, is VOC-free and remains as a homogeneous solution at low temperatures for an extended period of time.

Another object of the invention is to provide BIT compositions which can be included advantageously in latex, paint, coating, cosmetic and personal care products.

These and other objects of the invention will be made apparent from the following description of the invention.

SUMMARY OF THE INVENTION

What is described herein is a neutral pH, VOC-free biocidal composition consisting essentially of by weight, about 0.1-30%, 1,2-benzisothiazolin-3-one (BIT), about 20-90% polyethylene glycol (PEG) of molecular weight 400 or more, about 0-3%, preferably 1.5-2.5% sodium hydroxide (NaOH), KOH or LiOH and about 0-15%, preferably 5-10% water. These compositions are stable at temperatures as low as $-20°$ C. for an extended period of time. A preferred composition consists essentially of 20% BIT, 70% PEG-400, 2.1% NaOH and 7.9% water.

Such compositions are particularly useful in latex, paint, coating, cosmetic or personal care formulations.

DETAILED DESCRIPTION OF THE INVENTION

In accordance with the invention, there is provided herein a new and improved BIT composition, which is stable, has a neutral pH, is VOC-free and remains as a homogeneous solution even at low temperatures for an extended period of time.

The inventive features of the BIT composition herein is that, in combination, it has a neutral pH, so that it is particularly compatible with latex systems, i.e. it will not "shock" such formulations. Furthermore, it does not have any volatile component, i.e. it is VOC-free. Accordingly, the BIT composition herein does not include or need any cosolvent to prevent precipitation of the BIT. Large amounts of sodium hydroxide, which would increase the pH and solubility of BIT, are not needed or used herein. Also, xanthan gums, dispersants, and volatile organic solvents such as dipropylene glycol, alcohols, lower alkyl carbitols which contain odors, or other solvents such as tripropylene glycol or polypropylene glycol, which suffer from poor low temperature stability, are absent herein.

The combination of BIT and PEG-400 is VOC-free, and is a stable composition, whereas the use of PEG-300 gives only a volatile composition.

Most suitable BIT compositions of the invention consist essentially of, by weight, 0.1-30% BIT, 20-90% PEG-400 or more, 0-3%, preferably 1.5-2.5% NaOH, and 0-15%, preferably 5-10% water.

A preferred BIT composition of the invention consists essentially of 20% BIT, 70% PEG-400, 2.1% NaOH and 7.9% water.

The BIT composition herein is particularly useful in latex, paint, coating, cosmetic and personal care products.

A preferred formulation is a paint formulation.

The invention will now be described by reference to the following examples.

EXAMPLE 1

A composition of, by wt., 20.0% BIT (100%), 70.0% PEG-400, 10.0% 2.1% NaOH, pH=7.8 was subjected to a standard freeze-thaw test; it was stable for 10 cycles at −20° to 25° C.

EXAMPLE 2

The composition of Example 1 was tested as a biocide in PVA exterior white paint (PCL-717) having the formula given below:

PVA Exterior White: PCL-717 Formulation

| Ingredient | Amount (Pounds) | Amount (Gallons) |
| --- | --- | --- |
| Water | 50.0 | 6.00 |
| R&R 551 (Lecithin) | 4.4 | 0.5 |
| KTPP | 2.0 | 0.18 |
| Carbital Acetate | 8.4 | 1.00 |
| Propylene glycol | 27.9 | 3.00 |
| Foamacure AF 100 | 1.4 | 0.20 |
| Triton CF-10 | 4.4 | 0.50 |
| Cellosize QP 30,000 (2% solution) | 183.4 | 22.00 |
| Rutile TiO$_2$ R-960 | 225.0 | 6.61 |
| Nytal 300 | 100.0 | 4.22 |
| Duramite | 40.0 | 1.78 |
| W.G. Mica | 25.0 | 1.06 |

Ground above, then blend the following and add to above:

| | | |
| --- | --- | --- |
| Water | 25.0 | 3.00 |
| Foamacure AF 100 | 1.4 | 0.20 |

Blend the following with above under gentile agitation:

| | | |
| --- | --- | --- |
| UCAR 379G | 328.0 | 36.00 |
| Water | 114.7 | 13.70 |
| Total | 1141.0 | 99.95 |

Paint Constants:

| | |
| --- | --- |
| Viscosity, Initial | 72 K.U., 1200 cp |
| Weight/Gallon | 11.41 |
| P.V.C. | 42.5 |

The composition was very effective in protecting the paint from developing microbiological spoilage for an extended period of time.

While the invention has been described with particular reference to certain embodiments thereof, it will be understood that changes and modifications may be made which are within the skill of the art. Accordingly, it is intended to be bound only by the following claims, in which:

What is claimed is:

1. A latex, paint, coating, cosmetic or personal care formulation which comprises a neutral pH, VOC-free biocidal composition consisting of 20% 1,2-benzisothiazolin-3-one (BIT), 70% PEG-400, 2.1% NaOH and 7.9% water.

* * * * *